(12) United States Patent
Carr et al.

(10) Patent No.: US 11,684,493 B2
(45) Date of Patent: *Jun. 27, 2023

(54) ADJUSTABLE POSITION TRIAL COMPONENT WITH DRILL GUIDE

(71) Applicant: Smith & Nephew, Inc., Memphis, TN (US)

(72) Inventors: Christopher B. Carr, Bartlett, TN (US); Christopher R. Cyko, Memphis, TN (US); Dean Hughes, Cordova, TN (US); Jason S. Jordan, Hernando, MS (US)

(73) Assignee: Smith & Nephew, Inc., Memphis, TN (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/335,865

(22) Filed: Jun. 1, 2021

(65) Prior Publication Data

US 2021/0282941 A1 Sep. 16, 2021

Related U.S. Application Data

(63) Continuation of application No. 16/326,068, filed as application No. PCT/US2017/047288 on Aug. 17, 2017, now Pat. No. 11,045,332.

(Continued)

(51) Int. Cl.
*A61B 17/15* (2006.01)
*A61B 17/17* (2006.01)
(Continued)

(52) U.S. Cl.
CPC ........ *A61F 2/4684* (2013.01); *A61B 17/1764* (2013.01); *A61F 2/3859* (2013.01); *A61B 17/155* (2013.01)

(58) Field of Classification Search
CPC .......................... A61B 17/155; A61B 17/1764
See application file for complete search history.

(56) References Cited

U.S. PATENT DOCUMENTS 5,683,398 A * 11/1997 Carls .................... A61B 17/155
606/89
5,683,469 A 11/1997 Johnson et al.
(Continued)

FOREIGN PATENT DOCUMENTS

| CN | 1174498 A | 2/1998 |
|---|---|---|
| CN | 103260553 A | 8/2013 |
| CN | 103379880 A | 10/2013 |

OTHER PUBLICATIONS

First Office Action for Chinese Patent Application No. 201710708118.3 dated Feb. 3, 2020.
(Continued)

*Primary Examiner* — Nicholas W Woodall
(74) *Attorney, Agent, or Firm* — KDW Firm PLLC

(57) ABSTRACT

An exemplary trial component is configured to be attached to a resected bone having a resection surface, and includes a body portion and a sliding fastening mechanism movably coupled to the body portion. The body portion has an articular surface, a bone-facing surface, and at least one drill guide extending through the articular surface and the bone-facing surface. The sliding fastening mechanism includes at least one post extending beyond the bone-facing surface, and the post is operable to engage the resection surface to retain the position of the sliding fastening mechanism relative to the bone. When attached to the bone, the trial component is structured to selectively retain the position of the body portion relative to the bone, and to selectively permit adjustment of the position of the body portion relative to the bone.

15 Claims, 6 Drawing Sheets

Related U.S. Application Data

(60) Provisional application No. 62/376,333, filed on Aug. 17, 2016.

(51) Int. Cl.
*A61F 2/46* (2006.01)
*A61F 2/38* (2006.01)

(56) References Cited

U.S. PATENT DOCUMENTS

| | | | |
|---|---|---|---|
| 5,683,470 A | 11/1997 | Johnson et al. | |
| 5,720,752 A | 2/1998 | Elliot et al. | |
| 5,776,200 A | 7/1998 | Johnson et al. | |
| 7,695,520 B2 * | 4/2010 | Metzger | A61F 2/3859 623/20.35 |
| 8,603,101 B2 | 12/2013 | Claypool et al. | |
| 8,740,911 B2 | 6/2014 | Librot et al. | |
| 8,834,574 B2 | 9/2014 | Todd et al. | |
| 2004/0138670 A1 | 7/2004 | Metzger | |
| 2004/0153162 A1 * | 8/2004 | Sanford | A61B 17/1764 623/20.3 |
| 2005/0113840 A1 * | 5/2005 | Metzger | A61B 17/157 606/88 |
| 2006/0200158 A1 | 9/2006 | Fading et al. | |
| 2008/0119938 A1 | 5/2008 | Oh | |
| 2013/0013076 A1 | 1/2013 | Fisher et al. | |
| 2014/0094814 A1 * | 4/2014 | Hughes | A61B 17/1764 606/88 |

OTHER PUBLICATIONS

Chinese Search Report for Chinese Patent Application No. 201710708118.3 dated Feb. 3, 2020.
Second Office Action for CN Patent Application No. 201710708118. 3, dated Jan. 4, 2021, original and translated document, 20 pages.
Chinese Office Action; State Intellectual Property Office, Peoples Republic of China; Chinese Patent Application No. 201721032749. X; dated Jan. 25, 2019; 3 pages.
International Search Report; European Patent Office; International Application No. PCT/US2017/047288; dated Nov. 20, 2017; 4 pages.
Written Opinion of the International Searching Authority; European Patent Office; International Application No. PCT/US2017/047288; dated Nov. 20, 2017; 6 pages.

* cited by examiner

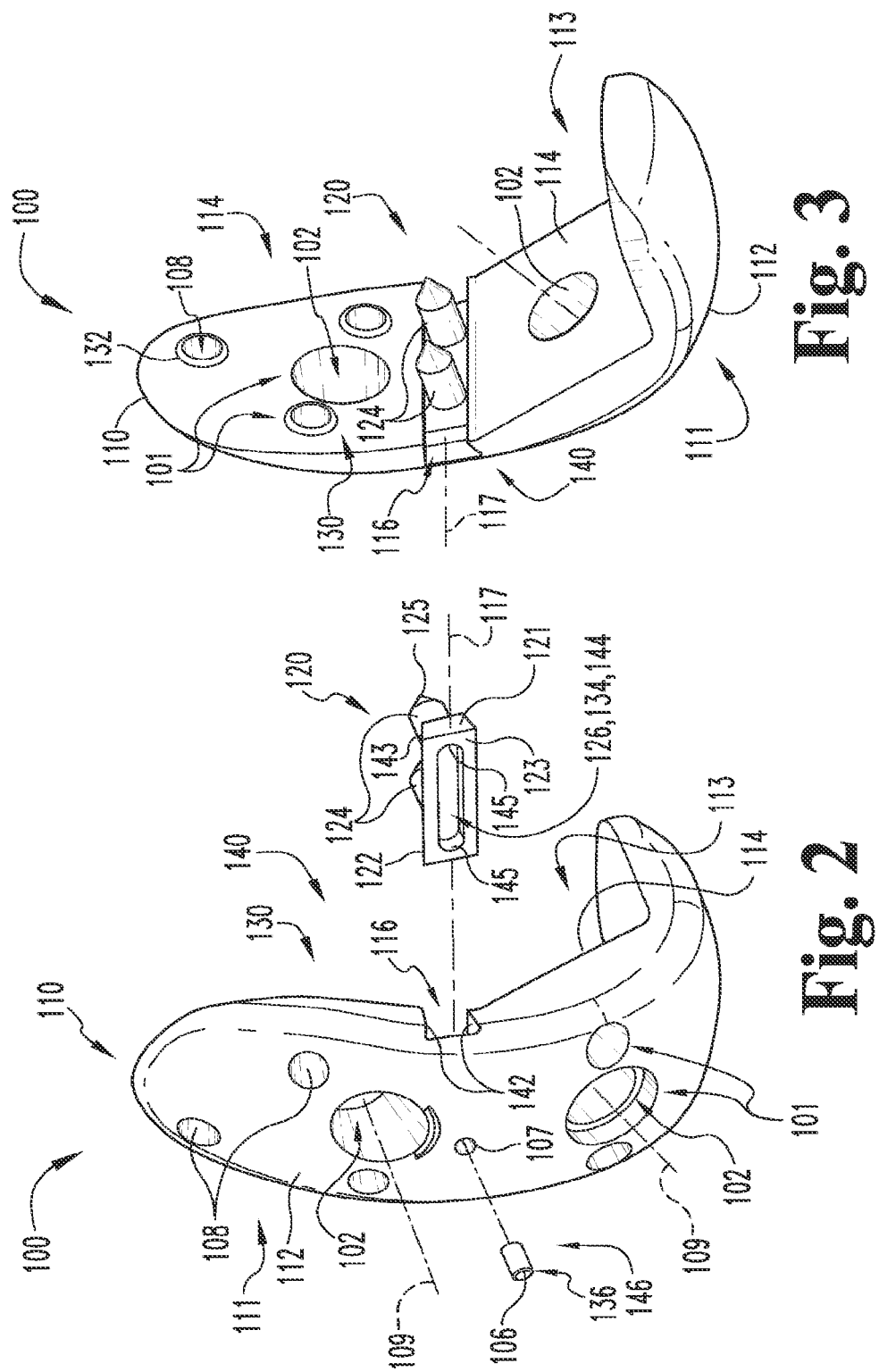

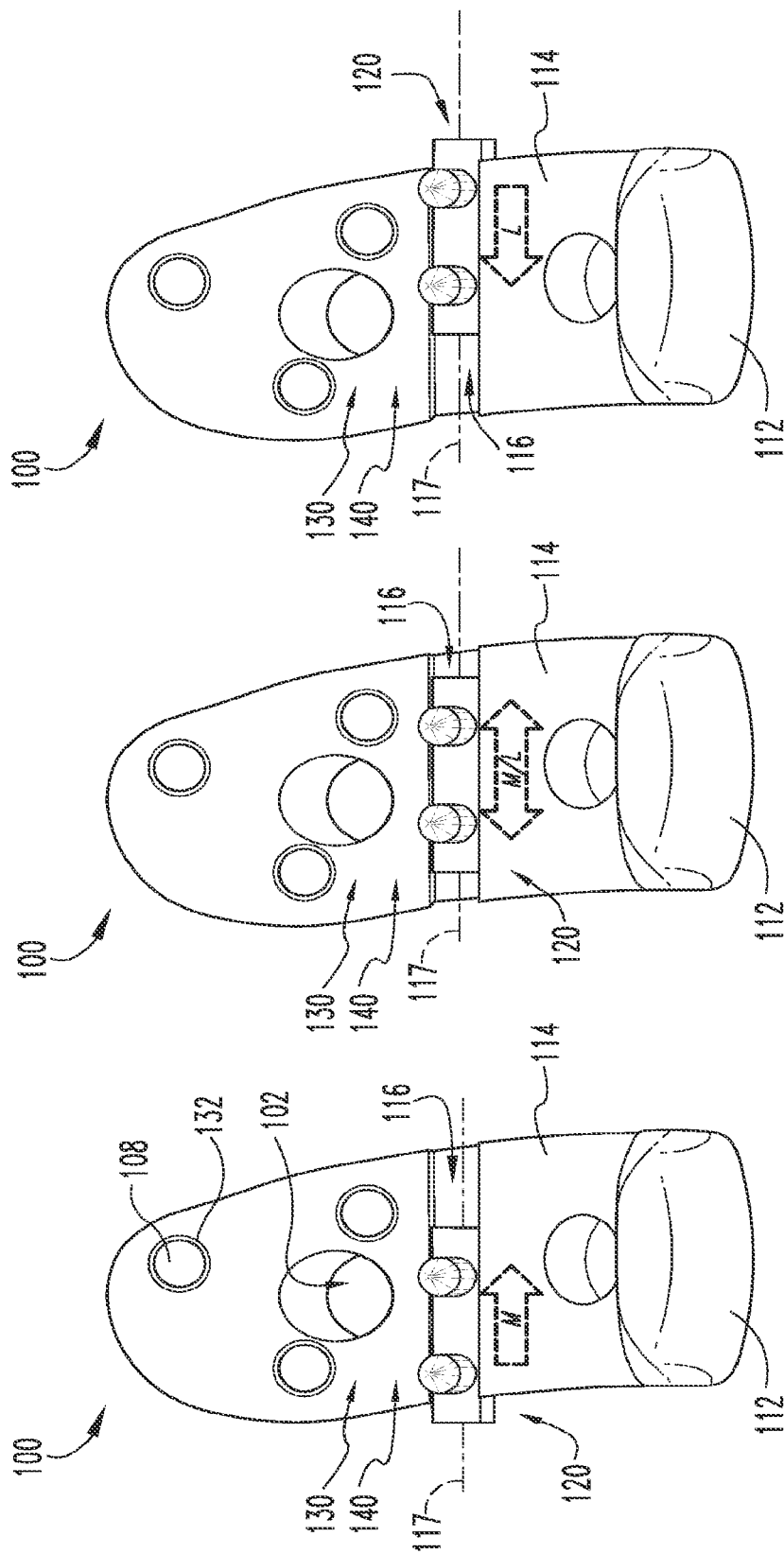

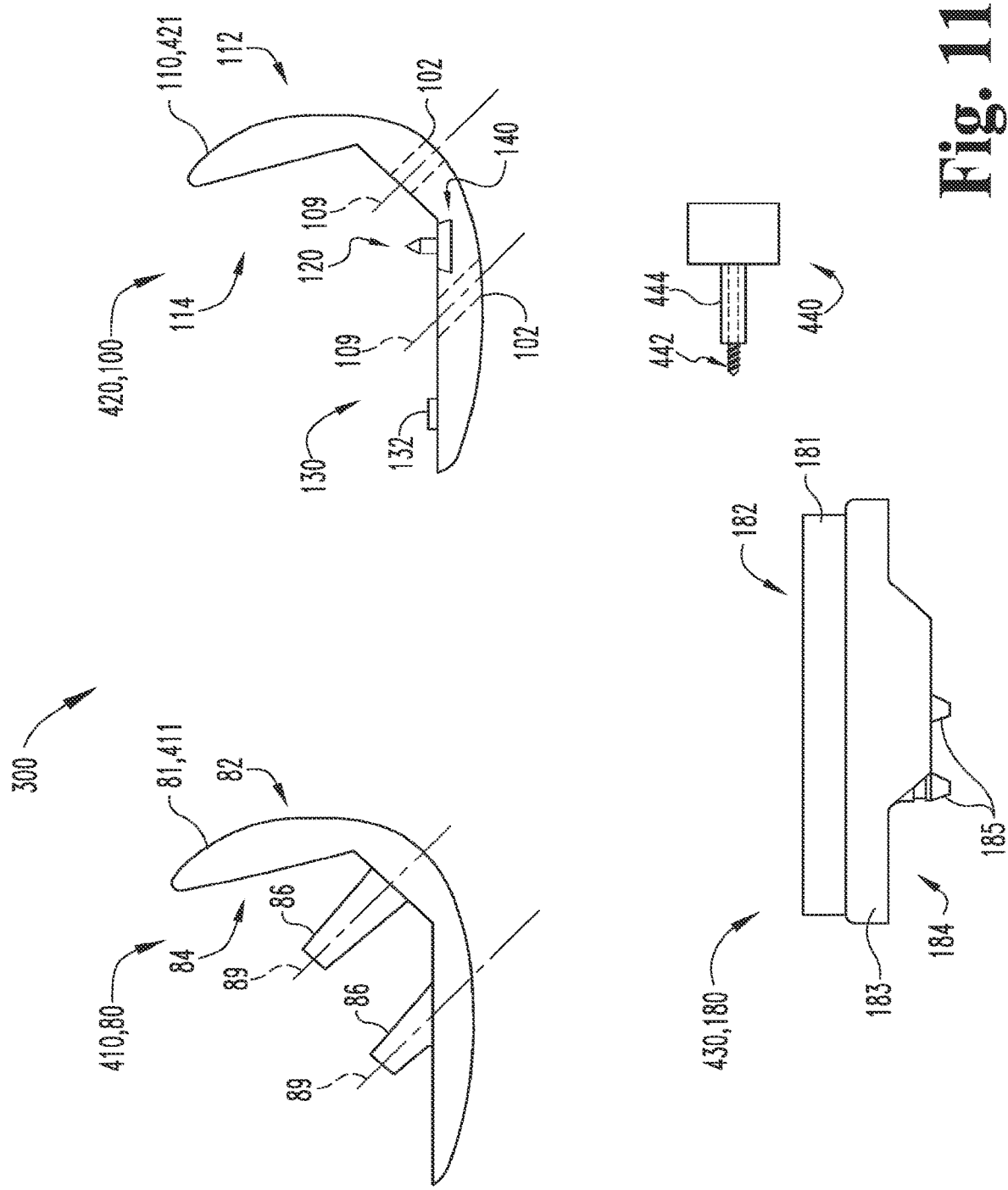

ADJUSTABLE POSITION TRIAL COMPONENT WITH DRILL GUIDE

CROSS-REFERENCE TO RELATED APPLICATION

The present application is a continuation of pending U.S. patent application Ser. No. 16/326,068, filed Feb. 15, 2019, which application is a U.S. National Phase filing of International Application No. PCT/US2017/047288, filed Aug. 17, 2017, which claims the benefit of U.S. Provisional Patent Application. No. 62/376,333, filed on Aug. 17, 2016. The contents of each of these applications are hereby incorporated by reference in their entirety.

TECHNICAL FIELD

The present disclosure generally relates to trial implants having adjustable positions, and more particularly but not exclusively relates to such trial implants which assist in preparation of cl bone for implantation of a final implant.

BACKGROUND

Unicondylar knee arthroplasty (UKA) is a surgical treatment option which may be utilized to address arthritic damage to a single compartment of the knee joint while maintaining the native cruciate ligaments. One aspect important for implant longevity when performing UKA is appropriate lateral/medial positioning of the femoral component such that it seats along the center of the tibial component during articulation, thereby reducing wear on the components. Additionally, an improperly positioned component may impede upon the soft tissue structures located anteromedially, which may result in discomfort or injury to the patient.

In certain conventional UKA procedures, lateral/medial positioning of the femoral component on the femur and its alignment relative to the tibial component are established at the stage in which the peg openings are formed in the resected femur. For example, one current technique involves the use of a non-articulating fixed block that includes both resection guide slots and drill guide holes, and the peg openings are drilled during the same stage as that in which the posterior and anterior resections are applied to the distal femur. Another current technique involves the use of a drill-through articulating trial component which is fixed to the femur by placing a pin in an aperture formed on the component. When placed, the pin protrudes beyond the articulating surface and precludes evaluation of the knee joint throughout its full range of movement (i.e., between full flexion and full extension). Such a complete evaluation is possible only after the peg openings have been drilled into the femur, a trial peg has been inserted into the drilled features, and the fixation pin has been removed.

As will be appreciated, once the peg holes have been formed in the femur, the lateral-medial position of the implant is set. In each of the techniques described above, however, complete evaluation of the performance of the implant is available only after the peg holes have been prepared. As such, the lateral-medial portion of the final femoral component cannot be adjusted despite the fact that the evaluation may indicate that the femoral component is not properly aligned with the tibial implant. For these reasons among others, a need remains for further improvements in this technological field.

SUMMARY

An exemplary trial component is configured to be attached to a resected bone having a resection surface, and includes a body portion and a sliding fastening mechanism movably coupled to the body portion. The body portion has an articular surface, a bone-facing surface, and at least one drill guide extending through the articular surface and the bone-facing surface. The sliding fastening mechanism includes at least one post extending beyond the bone-facing surface, and the post is operable to engage the resection surface to retain the position of the sliding fastening mechanism relative to the bone. When attached to the bone, the trial component is structured to selectively retain the position of the body portion relative to the bone, and to selectively permit adjustment of the position of the body portion relative to the bone. Further embodiments, forms, features, and aspects of the present application shall become apparent from the description and figures provided herewith.

BRIEF DESCRIPTION OF THE FIGURES

FIG. 2 is an exploded assembly view of a trial femoral component according to certain embodiments.

FIG. 3 is a perspective illustration of the trial femoral component illustrated in FIG. 2.

FIGS. 4A through 4C illustrate various states of the trial femoral component illustrated in FIG. 2.

FIG. 11 illustrates a surgical system according to certain embodiments.

DETAILED DESCRIPTION OF ILLUSTRATIVE EMBODIMENTS

Figure 1:
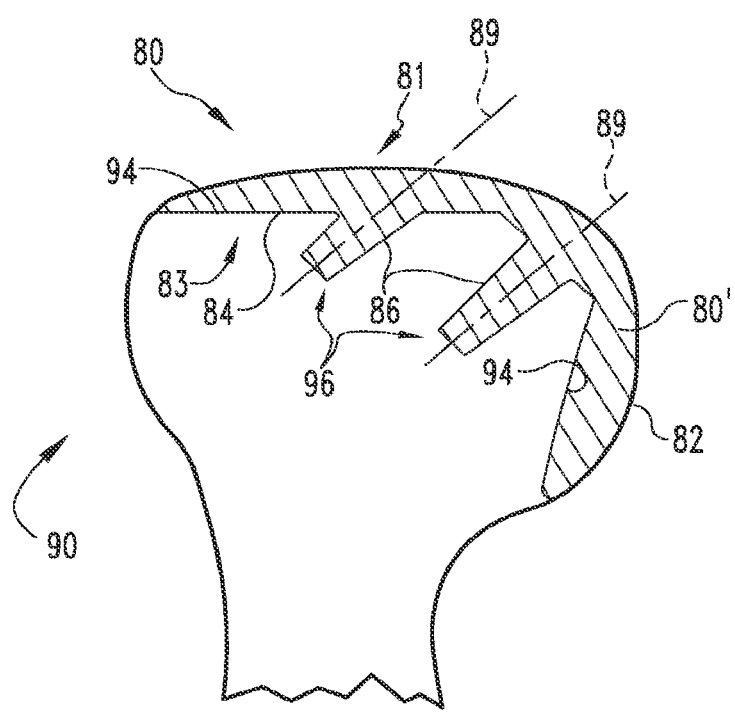
FIG. 1 is a cross-sectional illustration of a final femoral component implanted on a femur.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 illustrates a final femoral component 80 according to certain embodiments, and a surgically-prepared femur 90 on which the component 80 has been implanted. While other forms are contemplated, the illustrated femoral component 80 is provided in the form of a unicondylar component structured to replace at least a portion of a diseased, deteriorated, or otherwise damaged femoral condyle. The femoral component 80 includes a body portion 80', which includes an outer side 81 having an articular surface 82, and an inner side 83 having a bone-facing surface 84. The articular surface 82 is structured to mimic the articular surface of a healthy femoral condyle, and a bone-facing surface 84 is structured to engage the resection surfaces 94 generated during surgical preparation of the femur 90. The femoral component 80 also includes one or more pegs 86, each of which extends along a corresponding peg axis 89. Each peg 86 is received in a corresponding opening or peg hole 96 generated during surgical preparation of the femur 90, and aids in securing the component 80 to the femur 90.

With reference to FIGS. 2 and 3, illustrated therein is a trial femoral component 100 according to certain embodiments. The trial component 100 may be provisionally attached to the resected femur 90 to evaluate alignment, positioning, and/or kinematic performance characteristics prior to implantation of the final femoral component 80. The trial component 100 includes a body portion 110 and a sliding fastening mechanism in the form of a fastening slider 120, which is movably coupled to the body portion 110. As described in further detail below, the body portion 110 is configured to mimic the structure and performance of the final component 80, and the fastening slider 120 enables the lateral-medial (L/M) position of the body portion 110 to be adjusted while the trial component 100 is implanted to the femur 90. The illustrated trial component 100 also includes a selective coupling mechanism 130 configured to selectively prevent movement of the body portion 110 relative to the femur 90, and may further include a limiting mechanism 140 configured to limit the fastening slider 120 to a limited range of movement relative to the body portion 110.

The body portion 110 has an outer side 111 defining an articular surface 112, and an inner side 113 defining a bone-facing surface 114. The articular surface 112 is structured to mimic the articular surface of a healthy femoral condyle, and the bone-facing surface 114 is structured to engage the resection surfaces 94 generated during surgical preparation of the femur 90. The body portion 110 also defines a plurality of drill guides 101, which in the illustrated embodiment include peg drill guides 102 and fastener drill guides 108. As described herein, each of the drill guides 101 is structured to facilitate formation of fixation holes in the femur 90, and the fixation holes are configured to receive fixation devices for affixing the final component 80 to the femur 90.

The body portion 110 has a configuration corresponding to that of the final femoral component body portion 80' such that the structure and performance of the trial component 100 during trial evaluations substantially mimics the structure and performance of the final component 80. The inner side 113 includes a slide channel 116, which is defined in part by an opening in the bone-facing surface 114, and which extends along and defines a slide axis 117. When the trial component 100 is mounted to the resected femur 90, the slide channel 116 extends in the lateral and medial directions with respect to the anatomy of the patient, such that the slide axis 117 extends substantially in the same direction as the pivot axis about which the knee joint pivots.

The fastening slider 120 generally includes a slider body 122 having an outer first side 121 and an inner second side 123, and one or more posts 124 that extend from the second side 123 and define pointed tips 125. The slider body 122 is sized and configured to be received in the slide channel 110 such that the slider 120 is capable of movement along the slide axis 117. The slide channel 116 and the slider body 122 may have complementary geometries which restrict movement of the slider 120 to the lateral and medial directions, thereby preventing movement of the slider 120 in the direction along which the posts 124 extend. In the illustrated form, each of the slide channel 116 and the slider body 122 has a trapezoidal cross-section such that the outer first side 121 has a greater width than the inner second side 123, thereby providing a sliding dovetail connection between the slide channel 116 and the slider 120. It is also contemplated that other geometries may be utilized to restrict movement of the slider 120 to the lateral and medial directions, such as geometries including step-wise changes in the widths.

The outer first side 121 of the slider body 122 defines a slider channel 126, which extends along a portion of the lateral-medial length of the slider 120. In the illustrated form, the slider channel 126 is limited by a pair of end walls 127, which define the slider channel 126 as a closed channel. A pin 106 is mounted in an opening 107 formed in the body portion 110, and projects into the slider channel 126. As described herein, the pin 106 and slider channel 126 may be considered to at least partially define the selective coupling mechanism 130 and/or the limiting mechanism 140.

The selective coupling mechanism 130 is configured to selectively prevent movement of the body portion 110 relative to the femur 90 along the slide axis 117 when the trial component 100 is implanted. While other forms are contemplated, the illustrated selective coupling mechanism 130 is configured to selectively prevent movement of the body portion 110 relative to the femur 90 by discouraging or resisting such relative movement. In other words, the selective coupling mechanism 130 permits movement of the body portion 110 when a force along the slide axis 117 exceeds a threshold value, and prevents movement of the body portion 110 along the slide axis 117 in the absence of such a force exceeding a threshold value. It is also contemplated that the selective coupling mechanism 130 may selectively prevent movement of the body portion 110 relative to the femur 90 in additional or alternative manners, certain examples of which are set forth herein.

In certain forms, the selective coupling may be provided at least in part by direct engagement between the body portion 110 and the femur 90. For example, the illustrated selective coupling mechanism 130 includes a plurality of cleats 132, each of which is formed on the inner side 113 of the body portion 110 and projects inwardly beyond the bone-facing surface 114. When the trial component 100 is implanted to the femur 80, the cleats 132 engaged the resection surface 94 and discourage or resist movement of the body portion 110 along the slide axis 117, thereby contributing to the threshold force value. In the illustrated form, the cleats 132 are provided in the form of annular bosses, and each of the fastener drill guides 108 extends through a corresponding one of the cleats 132. It is also contemplated that the cleats 132 may be provided with another geometry, and that one or more of the cleats 132 may not necessarily have a drill guide 101 extending therethrough.

In certain embodiments, the selective coupling may be provided at least in part by indirect engagement between the body portion 110 and the femur 90. In the illustrated form, the selective coupling mechanism 130 provides for engagement between the body portion 110 and the slider 120, which in turn is engaged with the femur 90 when the trial component 100 is implanted. The selective coupling mechanism 130 may, for example, include a coupling channel 134 and a coupling member 136 that projects into the coupling channel 134. While other forms are contemplated, in the illustrated embodiment, the coupling channel 134 is provided as the slider channel 126, and the coupling member 136 is provided as the pin 106. The pin 106 may for example, be press fit into the slider channel 126 such that frictional forces resist but do not prevent relative movement of the body portion 110 and slider 120. As will be appreciated, selectively preventing relative movement of the body portion 110 and slider 120 contributes to selectively preventing movement of the body portion 110 relative to the femur 90 when the trial component 100 is implanted to the femur 90. In other words, the resistance to relative movement of the body portion 110 and slider 120 contributes to the threshold force value that must be exceeded to move the body portion 110 relative to the femur 90 when the trial component 100 is implanted.

While the illustrated coupling member 136 is provided as the press-fit pin 106, it is also contemplated that the coupling member 136 may be provided in another form. For example, the coupling member 136 may be provided in the form of a set screw which selectively prevents movement of the slider 120 along the slide axis 117. In such forms, the set screw may lock the L/M position of the slider 120 when engaged with the coupling channel 134 such that the set screw must be loosened in order to enable L/M movement of the slider 120. Additionally or alternatively, the set screw may resist L/M movement of the slider 120 without fully locking the slider 120 in position. In such embodiments, the set screw may function in a manner similar to that described above with respect to the press-fit pin 106, such that the set screw permits relative L/M movement of the body portion 110 and slider 120 only when an applied force along the slide axis 117 exceeds a threshold force value.

The illustrated limiting mechanism 140 is configured to constrain the slider 120 to movement along the slide axis 117. The limiting mechanism 140 may be considered to include the sidewalls 142 of the slide channel 116 and the corresponding sidewalls 143 of the slider body 122, which cooperate with one another to prevent movement of the slider 120 in directions orthogonal to the slide axis 117. While the illustrated limiting mechanism 140 includes the sliding dovetail connection provided by the mating trapezoidal cross-sections of the slide channel 116 and slider body 122, it is also contemplated that the mating geometries may be provided in another form, such as step-wise mating geometries.

The limiting mechanism 140 may further be configured to limit the slider 120 to a limited range of movement along the slide axis 117 such that the slider 120 is prevented from fully exiting the slide channel 116. For example, the limiting mechanism 140 may include a limiting channel 144 and a limiting member 146 that projects into the limiting channel 144. The limiting channel 144 extends in the direction of the slide axis 117, and is delimited by a pair of end walls 145. Each of the end walls 145 is configured to engage the limiting member 146 to prevent further movement of the slider 120 in a corresponding direction along the slide axis 117, thereby capturing the slider 120 with respect to the body portion 110. While other forms are contemplated, in the illustrated embodiment, the limiting channel 144 is provided as the slider channel 126, and the limiting member 146 is provided as the pin 106.

As is evident from the foregoing, engagement between the pin 106 and the slider channel 126 performs or contributes to at least two primary functions: selectively preventing movement of the body portion 110 relative to the femur 90 along the slide axis 117, and capturing the slider 120 with respect to the body portion 110. As such, the selective coupling mechanism 130 and the limiting mechanism 140 of the illustrated embodiment may each be considered to include the pin 106 and the slider channel 126. It is also contemplated that engagement between the pin 106 and the slider channel 126 may perform the functions associated with one of the mechanisms 130, 140, and the other of the mechanisms 130, 140, may include alternative features or may be omitted. By way of example, one or both of the end walls 145 may be omitted, and the pin 106 may selectively prevent relative movement of the body portion 110 and slider 120 without limiting the L/M travel range of the slider 120 in the lateral and/or medial directions. As another example, the pin 106 may serve to limit the lateral-medial travel of the slider 120 without significantly resisting movement of the slider 120 within the housed range of travel. In such forms, movement of the body portion 110 relative to the femur 90 may be selectively prevented by other features, such as the cleats 132.

FIGS. 4A through 4C illustrate the trial component 100 with the slider 120 in various positions with respect to the body portion 110. More specifically, FIG. 4A illustrates the slider 120 in a lateral terminal position, FIG. 4B illustrates the slider 120 in an intermediate position, and FIG. 4C illustrates the slider 120 in a medial terminal position. In the lateral terminal position (FIG. 4A), the slider 120 is movable in the medial direction indicated by the arrow. Additionally, the limiting member 144 may be engaged with one of the end walls 145 of the limiting channel 146, such that the limiting mechanism 140 prevents further movement of the slider 120 in the lateral direction. In the intermediate position (FIG. 4B), the slider 120 is movable in both the medial and lateral directions, as indicated by the double-ended arrow. In the medial terminal position (FIG. 4C), the slider 120 is movable in the lateral direction indicated by the arrow. Additionally, the limiting member 142 may be engaged with one of the end walls 145 of the limiting channel 144, such that the limiting mechanism 140 prevents further movement of the slider 120 in the medial direction.

While only three slider positions are illustrated in FIGS. 4A through 4C, it is to be understood that the slider 120 may be operable throughout a continuous range of lateral-medial positions along the slide axis 117, and the selective coupling mechanism 130 may selectively retain the slider 120 in each of these positions. As will be appreciated, relative L/M movement of the body portion 110 and slider 120 may equivalently be considered as movement of the body portion 110 in one of the lateral and medial directions and/or movement of the slider 120 in the other of the lateral and medial directions. For example, when the slider 120 is attached to the femur 90, lateral movement of the slider 120 with respect to the body portion 110 may be achieved by moving the body portion 110 in the medial direction while the slider 120 maintains constant position with respect to the femur 90.

Figure 5:
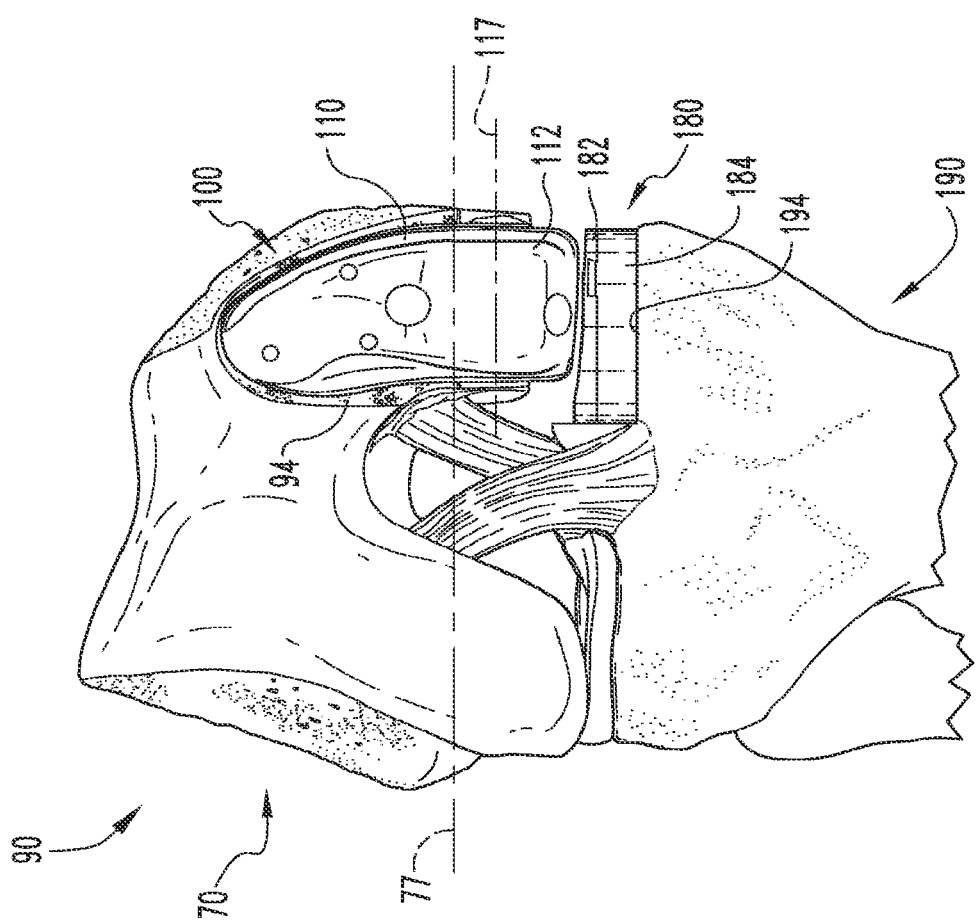
FIG. 5 illustrates of the trial femoral component illustrated in FIG. 2 attached to a resected distal femur and a tibial component attached to a resected proximal tibia.

FIG. 5 illustrates a knee joint 70 including the femur 90 and a tibia 190, along with the trial femoral component 100 and a tibial component 180. The knee joint 70 has a lateral-medial pivot axis 77 about which the femur 90 and tibia 190 pivot relative to one another during movement of the knee joint 70. In the illustrated state, the femur 90 and tibia 190 have been surgically prepared by resection, the trial femoral component 100 has been implanted to the resected femur 90, and the tibial component 180 has been implanted to the resected tibia 190. The tibial component 180 defines an articular surface 182 interfaced with the articular surface 112 of the femoral component 100, and a bone-facing surface 184 attached to a resection surface 194 of the tibia 190. In the illustrated form, the tibial component 180 is a final component which is fixedly attached to the tibia 190. In certain embodiments, the tibial component 180 may be a trial component, and may include features that enable the L/M position of the tibial component 180 to be adjusted. For example, the bone-facing surface 184 may include a channel similar to the above-described slide channel 116, and the tibial component 180 may further include a fastening slider similar to the above-described slider 120.

Figure 6:
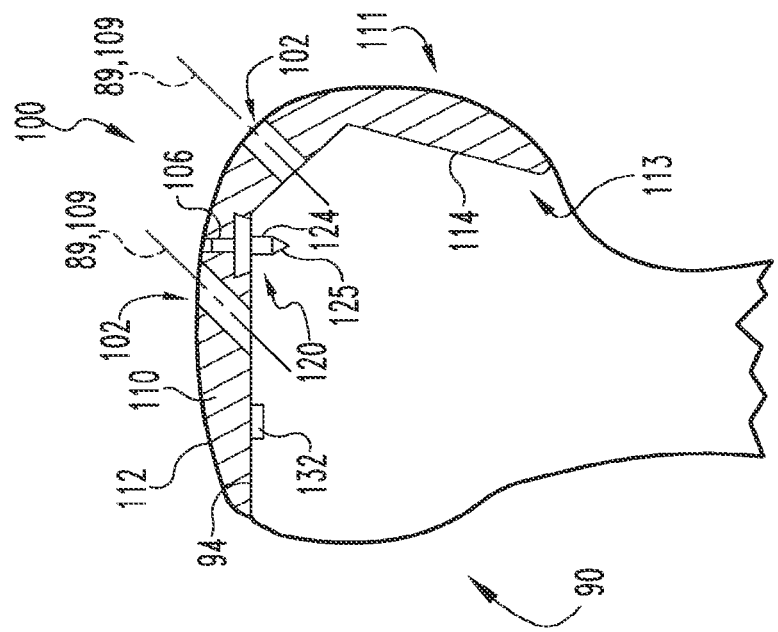
FIG. 6 is a cross-sectional illustration of the distal femur and attached trial femoral component illustrated in FIG. 5.

With additional reference to FIG. 6, illustrated therein is a cross-sectional view of the trial femoral component 100 attached to the femur 90. In this state, the selective coupling mechanism 130 selectively prevents movement of the body portion 110 relative to the femur 90. More specifically, the cleats 132 are engaged with the resection surface 94 and resist L/M movement of the body portion 110 with respect to the femur 90, and the posts 124 are engaged with the resection surface 94 and prevent L/M movement of the slider 120 with respect to the femur 90. Additionally, the frictional fit provided between the coupling member 134 and the coupling channel 136 resists relative L/M movement of the body portion 110 and the slider 120, thereby resisting L/M movement of the body portion 110 with respect to the femur 90.

With the trial component 100 implanted to the femur 90, the slide axis 117 extends generally parallel to the pivot axis 77 of the knee joint 70, thereby facilitating adjustment of the position of the body portion 110 along the pivot axis 77. Additionally, the selective coupling mechanism 130 resists L/M movement of the body portion 110 with respect to the femur 90. More specifically, the selective coupling mechanism 130 permits L/M movement of the body portion 110 when a force acting on the body portion 110 along the slide axis 117 exceeds a threshold force value, and prevents movement of the body portion 110 in the absence of such a force. In the illustrated form, both the frictional fit provided by the pin 106 and the engagement between the cleats 132 and the resection surface 94 contribute to the threshold force value. It is also contemplated that additional or alternative features may contribute to the threshold force value.

With the trial femoral component 100 and optionally the tibial component 180 implanted to the part 70, the alignment, positioning, and/or kinematic performance characteristics of the trial component 100 may be evaluated according to known techniques. During this evaluation, the selective coupling mechanism 130 retains the trial component 100 in the selected position. In the event that one of more of the characteristics is unsatisfactory, the L/M position of the trial component 100 may be adjusted by applying a lateral or medial force to the body portion 110 such that the lateral or medial force exceeds the threshold force value. As a result, the trial component 100 provides the ability to easily reposition the body portion 110 intra-operatively to an appropriate L/M position while still maintaining the original fixation points between the trial component 100 and resected femur 90 (i.e., the locations at which the posts 124 engage the resection surface 94).

In contrast to certain currently available trial components, the illustrated trial component 100 allows the surgeon to attach the drill-through femoral trial component 100 to the resected femur 90 without interrupting the articular surface 112. As a result, the illustrated trial component 100 enables a surgeon to check for correct alignment of the femoral component 100 relative to the tibial component 190 as the knee is actively moved through a full range of flexion and extension. Additionally, the illustrated trial component 100 utilizes a "floating" design which does not require removal of any fixation device for repositioning the body portion 110 during trialing and prior to preparing the femur 90 for the pegs 86, thereby facilitating positional adjustments prior to setting the position of the final femoral implant 80. The design of the trial component 100 and the floating nature of the slider 120 may enable adjustments to the medial-lateral position of the trial component 100 during the trialing stage, thereby facilitating positioning of the trial component 100 to be seated along the center of the tibial component 180 throughout the full range of articulation.

When the L/M position of the trial component 100 is determined to be satisfactory, the trial component 100 may assist in preparing the femur 90 for implantation of the final component 80. In the illustrated form, the central axis 109 of each peg drill guide 102 is coincident with the axis 89 along which a corresponding one of the pegs 86 will extend when the final component 80 is implanted. Accordingly, each peg drill guide 102 may be utilized to align a drill bit with the corresponding axis 89, 109, and the drill bit may be driven to form a corresponding one of the peg holes 96. Additionally or alternatively, one or more of the fastener drill guides 108 may be used as a guide to drill pilot holes in the femur 90, for example in embodiments in which the final component 80 is to be attached to the femur 90 using fasteners in addition or as an alternative to the pegs 86. In either event, the threshold force value provided by the attached trial component 100 may facilitate the retention of the body portion 110 in the selected position relative to the femur 90 during the drilling. This may ensure that the drilled holes are formed in the correct locations in the femur 90 such that the fatal component 80 can be implanted in the position which was deemed satisfactory during the trial stage.

As is evident from the foregoing, when the illustrated trial component 100 is attached to the resected femur 90, the selective coupling mechanism 130 selectively retains the body portion 110 in the selected position. More specifically, the attached trial component 100 prevents movement of the body portion 110 relative to the femur 90 until an applied lateral or medial force exceeds the threshold force value. As will be appreciated, selection of the threshold force value may involve weighing competing concerns relating to the appropriate level of resistance provided by the attached trial component 100. For example, a desire for the trial component 100 to maintain its position during the evaluation and drilling stages may weigh in favor of a higher threshold force value, while a desire for easier adjustment of the L/M position of the body portion 110 may weigh in favor of a lower threshold force value.

In certain embodiments, at least one factor contributing to the threshold force value may be set pre-operatively. As one example, the geometry and configuration of the cleats 132 may be selected to provide a desired resistance to movement of the body portion 110 relative to the femur 90. As another example, the structure and press-fitting of the pin 106 may be selected such that the frictional fit between the coupling channel 134 and the coupling member 136 provides a desired resistance to relative movement of the body portion 110 and the slider 120 along the slide axis 117. In certain embodiments, one or more factors contributing to the threshold force value may be adjusted intra-operatively. By way of example, in embodiments in which the coupling member 136 is provided in the form of a set screw, the resistance to relative L/M movement of the body portion 110 and slider 120 may be adjusted by loosening or tightening the set screw.

FIGS. 7-10 illustrate trial components 200, 300 according to further embodiments. Each of the trial components 200, 300 is substantially similar to the trial component 100 described above with reference to FIGS. 2-6. Unless indicated otherwise, similar reference characters are used to indicate similar elements and features. For example, the trial component 200 illustrated in FIGS. 7 and 8 includes a body portion 210, a sliding fastening mechanism 220 including two posts 224, a selective coupling mechanism 230 selectively coupling the body portion 210 and the fastening mechanism 220, and a limiting mechanism 240 limiting relative movement of the body portion 210 and the fastening mechanism 220. Similarly, the trial component 300 illustrated in FIGS. 9 and 10 includes a body portion 310, a sliding fastening mechanism 320 including two posts 324, a selective coupling mechanism 330 selectively coupling the body portion 310 and the fastening mechanism 320, and a limiting mechanism 340 limiting relative movement of the body portion 310 and the fastening mechanism 320. In the interest of conciseness, the following descriptions focus primarily on features that are different from those described above with regard to the trial component 100. It is to be understood, however, that the trial components 200, 300 may include various features analogous so those described above with reference to the trial component 100, such as one or more drill guides 101 and/or one or more cleats 132.

Figure 7:
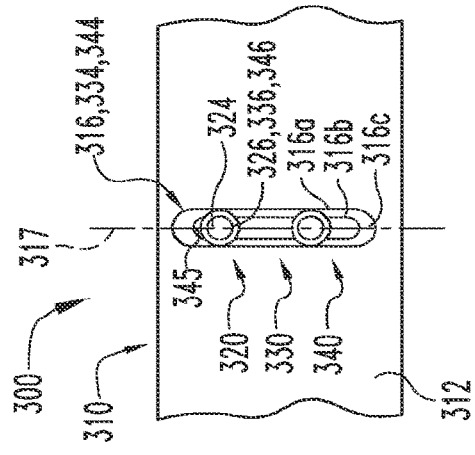
FIGS. 7 and 8 illustrate a trial component according to another embodiment.
Figure 8:
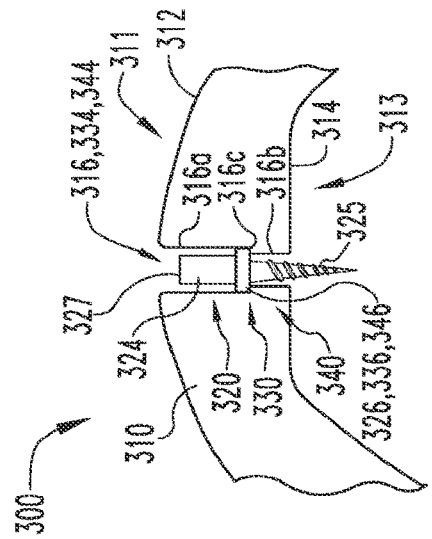

With specific reference to FIGS. 7 and 8, the trial component 200 includes a slide channel in the form of a slot 216, which extends through the body portion 210 between the articular side 212 and the bone-facing side 214. When placed on the resected femur 90, the body portion 210 may be provisionally attached to the femur 90 with the sliding fastening mechanism 220. For example, the posts 234 may be inserted into the slot 216 such that the pointed tips 225 engage the resection surface 94, and may be tapped into engagement with the femur 90 using a hammer. With the posts 224 implanted, the ends 227 opposite the tips 225 do not extend beyond the articular surface 212, thereby maintaining the continuity of the articular surface 212 and enabling trial evaluations throughout a full range of extension and flexion. In certain forms, the posts 224 may be recessed relative to the articular surface 212, which may, for example, be achieved by placing a rod in abutment with the end 227 of the post 224, and tapping the rod with the hammer.

In certain embodiments, engagement of the posts 224 with the body portion 210 may resist movement of the body portion 210 relative to the sliding fastening mechanism 220, thereby contributing to the threshold force value provided by the selective coupling mechanism 230. By way of example, the diameters of the post 224 may be slightly larger than the width of the slot 216, such that a frictional fit is formed between the posts 224 and the body portion 210. In other embodiments, the sliding fastening mechanism 220 may not necessarily contribute to the threshold force value, and the selective retention of the body portion 210 relative to the femur 90 may be provided by other features, such as cleats.

In the illustrated form, the coupling channel 234 is defined by the slide slot 216, and the coupling member 236 is defined by the posts 224. Similarly, the limiting channel 244 is provided by the slot 216, and the limiting member 246 is defined by the posts 244. The slot 216 has a constant width through the thickness of the body portion 210, thereby enabling the frictional fit to be formed along at least a portion of the length each post 224. It is also contemplated that the width of the slot 216 may taper inward from the articular side 213 to the bone-facing side 214. The greater width at the outer side 211 may facilitate insertion of the posts 224, while the smaller width at the inner side 213 may provide for a frictional fit between the posts 224 and the body portion 210. Additionally, while the illustrated body portion 210 defines a single slot 216, it is also contemplated that two discrete slots may be formed, such that each post 224 is received in a corresponding one of the slots.

Figure 9:
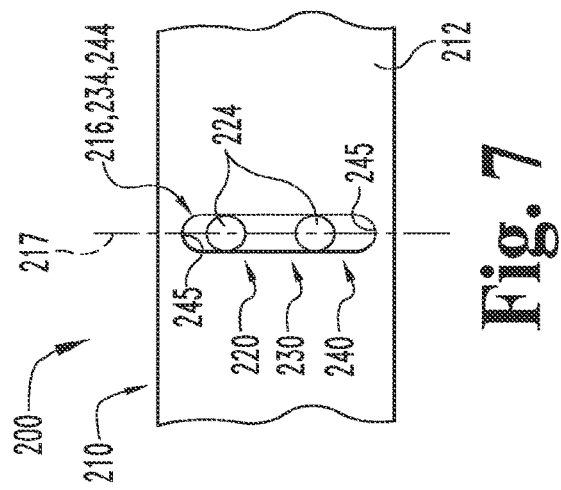
FIGS. 9 and 10 illustrate a trial component according to another embodiment.
Figure 10:
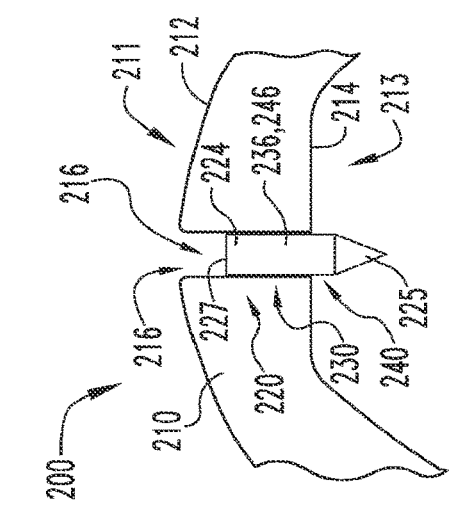

With specific reference to FIGS. 9 and 10, the body portion 310 of the trial component 300 includes a slide channel in the form of a slot 316, which extends between the articular surface 312 and the bone-facing surface 314. In contrast to the above-described slot 216, the slot 316 of the instant embodiment is provided in the form of a stepped slot having a wider outer portion 316a and a narrower inner portion 316b, and a ledge 316c is formed at the interface of the wider portion 316a and the narrower portion 316b. Each of the posts 324 includes a collar 326 having a diameter greater than the width of the narrower portion 316b such that the collars 326 are supported by the ledge 316c. Each post 324 also includes a threaded tip 325 operable to engage the resected femur 90, and an opposite end 327 received within the slot 316.

When placed on the resected femur 90, the body portion 310 may be provisionally attached to the femur 90 with the sliding fastening mechanism 320. For example, the screw posts 324 may be inserted into the slot 316 such that the threaded tips 325 engage the resection surface 94. When the screw posts 324 are rotated, the threaded tips enter the femur 90, and the collar 326 acts on the ledge 316c to urge the bone-facing surface 314 into contact with the resection surface 94. While the illustrated body portion 310 defines a single slot 316, it is also contemplated that two discrete slots may be formed, such that each post 324 is received in a corresponding one of the slots.

As in the above-described embodiments, when the trial component 300 is implanted to the femur 90, the selective coupling mechanism 330 selectively retains the position of the body portion 310 relative to the femur 90, and the limiting mechanism 340 limits relative movement of the body portion 310 and the fastening mechanism 320. More specifically, the selective coupling mechanism 330 selectively prevents L/M movement of the body portion 310 when an L/M force acting on the body portion 310 falls below a threshold force value, and selectively permits L/M movement of the body portion 310 when the L/M force exceeds the threshold force value. As will be appreciated, tightening the screw posts 324 may increase frictional forces between the bone-facing surface 314 and the resection surface 94, as well as frictional forces between the collar 326 and the ledge 316c. Accordingly, the threshold force value may be adjusted by tightening or loosening the screw posts 324.

In certain embodiments, the screw posts 324 may initially be tightened to a degree sufficient to provide a selected threshold force value, such that the L/M position of the body portion 310 can be selectively adjusted without loosening the screw posts 324. In other embodiments, the screw posts 324 may initially be tightened to a degree sufficient to maintain their positions without significantly engaging the ledge 316c, thereby enabling free L/M travel of the body portion 310 within the limited range provided by the limiting mechanism 340. In either event, the screw posts 324 may be tightened to a degree sufficient to retain the body portion 310 in place during the trial evaluation. If warranted, the L/M position can subsequently be adjusted. In certain forms, adjusting the L/M position of the body portion 310 after a trial evaluation may require loosening one or more of the screw posts 324. In other forms, the screw posts 324 may have been tightened only to the degree necessary to maintain the position of the body portion 310 during the trial evaluation without fully locking the position of the body portion 310. In such embodiments, adjusting the L/M position of the body portion 310 may include applying a force above the threshold force value without loosening the screw posts 324.

FIG. 11 illustrates a surgical system 400 according to certain embodiments. The system 400 includes a final component 410 including a final body portion 411 and a trial component 420 including a trial body portion 421 having an overall geometry corresponding to that of the final body portion 411. The outer and inner surfaces of the body portions 411, 421 are substantially similar to one another such that the trial component 420 mimics the structure and performance of the final component 410. Thus, while the illustrated trial body 421 has drill guides 102 and cleats 132 which are not present in the final body 411, the body portions 411, 421 may nonetheless be considered to have corresponding overall geometries, so long as the performance of the trial component 420 during trial evaluations is not materially different than the performance of the final component 410 when implanted.

With additional reference to FIGS. 2-6, the final component 410 of the illustrated system 400 is provided in the form of the above-described final femoral component 80, and the trial component 420 is provided in the form of the above-described trial femoral component 100. It is also contemplated that one or both of the components 410, 420 may be provided in another form. By way of example, the trial component 420 may instead be provided in the form of the trial component 200 or the trial component 300. Additionally, while the components 80, 100 are described above as configured for use in a unicondylar knee arthroplasty (UKA), it is also contemplated that the components 410, 420 of the system 400 may be configured for use in another form of orthopedic procedure, such as a total knee arthroplasty (TKA) or another form of arthroplasty.

The surgical system 400 may further include a second final component 430 configured to provide an articular surface along which each of the final component 410 and the trial component 430 may articulate. While other forms are contemplated, the second final component 430 of the illustrated embodiment is provided in the form of the above-described tibial component 180.

The surgical system 400 may further include a drill 440 having a rotating bit 442. The bit 442 may extend through a sleeve 444 such that the sleeve 444 partially encloses the bit 442. The sleeve 444 may have an outer diameter corresponding to the inner diameter of the peg drill guides 102 such that when the sleeve 444 is received in the peg drill guide 102, the bit 442 extends along the axis 109 of the peg drill guide 102. When so aligned, the drill 440 may be activated to form peg holes 96 in the femur 90 to which the trial component 100, 420 is attached. Due to the fact that the drill guide axes 109 correspond to the peg axes 89, the peg holes 86 will be formed in the appropriate locations to receive the pegs 86. The diameter of the drill bit 442 may be slightly less than a diameter of the pegs 86 such that a frictional fit is formed between the pegs 86 and the femur 90.

With the pegs 86 of the final component 80 received in the peg holes 96, the position of the implanted final component 80, 410 corresponds to the position of the trial component 100, 420 at the time the peg holes 86 were formed. As noted above, the peg holes 96 may be formed at the time the trial component 100 is found to exhibit satisfactory positioning and performance characteristics. Additionally, the final component 80, 410 and trial component 100, 420 are structured such that the performance of the knee joint 70 with the trial component 100, 420 implanted substantially mimics performance of the knee joint 70 with the final component 80, 410 implanted. Thus, upon implanting the final component 80, 410, the knee joint 70 will exhibit the positioning and performance characteristics deemed to be satisfactory during evaluation of the trial component 100, 420.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. An orthopedic trial component configured to provisionally replace a portion of a bone of a joint, the orthopedic trial component comprising:
   a body portion comprising:
      an outward-facing side defining an articular surface for the joint;
      an inward-facing side defining a bone-facing surface configured to abut a resection surface of the bone;
      a slide channel formed in the inward-facing side of the body portion, wherein the slide channel extends along a slide axis, and is defined in part by an opening in the bone-facing surface; and
      at least one drill guide extending from the articular surface to the bone-facing surface in a predetermined orientation relative to the body portion;
   a slider body arranged and configured to be at least partially positioned within the slide channel, the slider body being arranged and configured to be slidably moveable with the slide channel along the slide axis, at least a portion of the slider body extending through the opening formed in the bone-facing surface to contact the resection surface of the bone in use;
   a pin arranged and configured to interact with a channel formed in a rear surface of the slider body to selectively prevent movement of the slider body along the slide axis; and
   a limiting mechanism configured to provide the slider body with a limited range of movement along the slide axis, wherein the limiting mechanism comprises a pair of end walls delimiting the channel, and wherein each of the end walls is configured to contact the pin to define a corresponding terminal position for the limited range of movement.

2. The orthopedic trial component of claim 1, wherein the pin is engaged with the channel via a frictional fit, and wherein frictional fit discourages relative movement of the slider body and the body portion, thereby preventing movement of the slider body relative to the body portion in the absence of a force along the slide axis exceeding a threshold value.

3. The orthopedic trial component of claim 1, wherein the pin is configured to permit movement of the body portion when a force along the slide axis exceeds a threshold force value, and to prevent movement of the body portion when the force along the slide axis does not exceed the threshold force value.

4. The orthopedic trial component of claim 3, wherein the threshold force value is sufficient to retain the body portion in a selected position throughout a full range of flexion and extension of the joint.

5. The orthopedic trial component of claim 1, wherein the body portion includes an opening formed therein for receiving the pin.

6. The orthopedic trial component of claim 5, wherein the opening extends from the articular surface of the body portion into the slide channel.

7. The orthopedic trial component of claim 1, wherein the slide channel is configured such that the slide axis extends parallel to a pivot axis of the joint when the orthopedic trial component is implanted to the bone.

8. The orthopedic trial component of claim 1, further comprising at least one cleat projecting beyond the bone-facing surface, the at least one cleat configured to engage the resection surface of the bone to discourage movement of the body portion relative to the bone.

9. The orthopedic trial component of claim 8, wherein at least one of the drill guides extends through a corresponding one of the at least one cleat.

10. An orthopedic trial component, comprising:
   a body portion comprising:
      an outer side defining an articular surface;
      an inner side defining a bone-facing surface;
      a slide channel extending along a slide axis; and
      at least one drill guide extending from the articular surface to the bone-facing surface in a predetermined orientation relative to the body portion;
   a sliding fastening mechanism including a slider body slidably received within the slide channel, the slider body including a channel formed in a rear surface thereof, the pin interacting with the channel, and at least one bone-engaging post extending beyond the bone-facing surface;
   a selective coupling mechanism configured to selectively prevent movement of the sliding fastening mechanism along the slide axis, the selective coupling mechanism comprising an opening formed in the body portion extending from the articular surface to the slide channel and a pin selectively insertable into the opening and into contact with the sliding fastening mechanism; and
   a limiting mechanism configured to limit the slider body to a limited range of movement along the slide axis, the limiting mechanism comprising a first end wall and a second end wall delimiting the channel, the pin arranged and configured to contact each of the end walls to limit the range of movement in a corresponding direction along the slide axis.

11. The orthopedic trial component of claim 10, wherein each of the at least one bone-engaging posts is coupled to the slider body.

12. The orthopedic trial component of claim 10, further comprising at least one cleat projecting beyond the bone-facing surface, the at least one cleat configured to engage a patient's bone to discourage movement of the body portion relative to the patient's bone.

13. The orthopedic trial component of claim 12, wherein at least one of the drill guides extends through a corresponding one of the at least one cleat.

14. The orthopedic trial component of claim 10, wherein the selective coupling mechanism is configured to permit movement of the body portion when a force along the slide axis exceeds a threshold force value, and to prevent movement of the body portion when the force along the slide axis does not exceed the threshold force value.

15. The orthopedic trial component of claim 14, wherein the threshold force value is sufficient to retain the body portion in a selected position throughout a full range of flexion and extension of the joint.

* * * * *